United States Patent [19]

Burkart et al.

[11] Patent Number: 4,939,165
[45] Date of Patent: Jul. 3, 1990

[54] PHOTOACTIVE BITHIENYL PESTICIDES

[76] Inventors: Susan E. Burkart, 1414 Dutch Neck-Edinburg Rd., Trenton, N.J. 08691; Richard B. Phillips, 2213 Cherrytree Lane, Riverbank, Calif. 95367; David M. Roush, 322 Ewing St., Princeton, N.J. 08540

[21] Appl. No.: 317,105

[22] Filed: Feb. 28, 1989

Related U.S. Application Data

[63] Continuation-in-part of Ser. No. 120,781, Nov. 13, 1987, abandoned, which is a continuation-in-part of Ser. No. 56,353, May 27, 1987, abandoned, which is a continuation of Ser. No. 842,707, Mar. 20, 1986, abandoned, which is a continuation-in-part of Ser. No. 724,224, Apr. 17, 1985, Pat. No. 4,645,777.

[51] Int. Cl.$^5$ .................... A01N 43/02; C07D 409/00
[52] U.S. Cl. .................................... 514/444; 549/59; 71/90
[58] Field of Search ............... 549/59; 514/444; 71/90

[56] References Cited

U.S. PATENT DOCUMENTS 3,050,442  8/1962  Bijloo et al. ............................ 71/90
4,645,777  2/1987  Burkart et al. ...................... 514/444

FOREIGN PATENT DOCUMENTS 50-37256  3/1986  Japan .

OTHER PUBLICATIONS

Bedell, et al., *J. Org. Chem.*, 27, 2026 (1962).
Chem. Abstr., 97, 182136g (1982).
Gommers et al., *Photochem. and Photobiol.*, 35, 615 (1982).
Kagan, et al., *Experientia*, 37, 80 (1981).
Stetter, et al., *Chem. Ber.*, 114, 581 (1981).
Stetter, et al., *J. Heterocyclic Chem.*, 14, 573 (1977).
Wynberg, et al., *Syn. Comm.*, 14, 1 (1984).

Primary Examiner—Alan Siegel
Attorney, Agent, or Firm—Robert L. Anderson; H. Robinson Ertelt

[57] ABSTRACT

Bithienyl compounds of the following structural formula are phototoxic insecticides and acaricides:

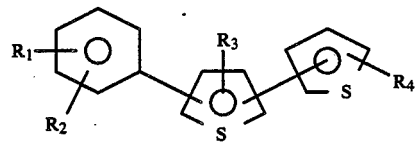

wherein
$R_1$ is selected from hydrogen, halogen, alkyl, haloalkyl, alkoxy, haloalkoxy, haloalkenoxy, phenyl, phenoxy, nitro, alkylsulfinyl, alkylsulfonyl, and alkylthio provided $R_4$ is other than hydrogen;
$R_2$ is selected from hydrogen and halogen, or $R_1$ and $R_2$ at adjacent positions are joined to form $C_4H_4$;
$R_3$ is selected from hydrogen, alkyl, thienyl, and phenyl optionally substituted with alkyl, alkoxy, or 1-2 halogen; and
$R_4$ is selected from hydrogen, halogen, alkyl, haloalkyl, alkoxy, alkylthio, alkylsulfinyl, haloalkenylthio, formyl, alkylcarbonyl, alkoxycarbonyl, phenylcarbonyl, dialkylphosphono, and nitro.

7 Claims, No Drawings

PHOTOACTIVE BITHIENYL PESTICIDES

This application is a continuation in part, of application Ser. No. 120,781, filed Nov. 13, 1987, now abandoned, which is a continuation-in-part of 056,353, filed May 27, 1987, now abandoned, which is a cont. of 842,707, filed 3/20/86, now abandoned, which is a continuation in part of application Ser. No. 724,224 filed Apr. 17, 1985 now U.S. Pat. No. 4,645,777.

This invention is in the field of bioaffecting heterocyclic organic chemical compounds which contain a bithienyl nucleus. More particularly, the invention includes certain bithienyl compounds per se, agricultural compositions containing the novel compounds, and the method of using a broad class of bithienyl compounds to control insects and acarids.

U.S. Pat. No. 3,050,442 discloses certain 60-polythienyl compounds, including 5-phenyl-2,2'-bithienyl, and the utility of such compounds as nematicides. The phytotoxicity of the polythienyls is also disclosed and exemplified. The possible effect of light on the biological activity of the compounds is not mentioned.

The activity of certain polythienyl compounds, including 5-phenyl-2,2'-bithienyl, against a specific nematode injurious to pine is disclosed in Japanese Kokai 50-37256.

5-Phenyl-2,2'-bithienyl is reported to be phototoxic to *Candida utilis*, a fungus; see *Experimentia*, 37, 80 (1981). It was recently reported on the basis of non-foliar tests that 5-phenyl-2,2'-bithienyl is a photodynamic nematicide; see *Photochem. Photobiol.*, 35, 615 (1982).

The phytotoxicity attributed to 5-phenyl-2,2'-bithienyl by earlier workers discourages testing this compound as a foliar insecticide or acaricide on plant crops. Notwithstanding this, according to the present invention, 5-phenyl-2,2'-bithienyl is effective against foliage-feeding insects and acarids, especially under irradiation with near ultraviolet light, plentifully available in sunlight. Furthermore, certain derivatives of 5-phenyl-2,2'-bithienyl are more effective as photoactive foliar insecticides and acaricides than the unsubstituted parent compound. Taking advantage of the activity levels attained in sunlight, the bithienyl compounds can be applied to the foliage at such low rates that phytotoxicity is not a problem.

The photoactive bithienyl compounds of this invention are represented by the following structural formula:

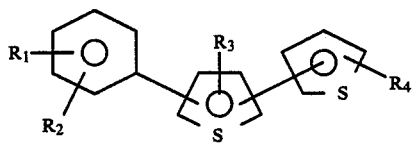

wherein $R_1$ is selected from hydrogen, halogen, alkyl, haloalkyl, alkoxy, haloalkoxy, haloalkenoxy, phenyl, phenoxy, nitro, alkylsulfinyl, alkylsulfonyl, and alkylthio provided $R_4$ is other than hydrogen; $R_2$ is selected from hydrogen and halogen, or $R_1$ and $R_2$ at adjacent positions are joined to form $C_4H_4$; $R_3$ is selected from hydrogen, alkyl, thienyl, and phenyl optionally substituted with alkyl, alkoxy, or 1-2 halogen; and $R_4$ is selected from hydrogen, halogen, alkyl, haloalkyl, alkoxy, alkylthio, alkylsulfinyl, haloalkenylthio, formyl, alkylcarbonyl, alkoxycarbonyl, phenylcarbonyl, dialkylphosphono, and nitro.

The terms "halo" and "halogen" when employed herein mean fluorine, chlorine or bromine. The terms "alkyl," "alkenyl" and "alkoxy" imply a straight or branched hydrocarbon chain, preferably containing 1–6, especially 1–4, carbon atoms; "halo+" coupled with either term means one or more hydrogen atoms has been replaced by halogen.

Among the bithienyl compounds encompassed by the aforesaid structural formula, those wherein at least one of $R_1$, $R_2$, $R_3$, and $R_4$ is other than hydrogen or alkyl are new compounds. The most active compounds are those wherein $R_1$ is a 4-substituent, especially halogen or haloalkyl, e.g., fluorine or trifluoromethyl; $R_2$ and $R_3$ are hydrogen; and $R_4$ is hydrogen, halogen, alkyl, alkylthio, alkylsulfinyl, haloalkenylthio, formyl, alkoxycarbonyl, and -phenylcarbonyl. In general, the greatest activity is displayed by those isomers having a 5-phenyl-2,2'-bithienyl nucleus. in which $R_1$ is in the 4 position and $R_4$ is in the 5 position.

Particularly preferred are compounds of the formula:

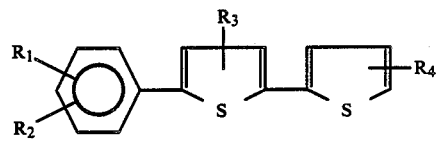

in which:
(a) $R_1$, $R_2$, and $R_3$ are hydrogen and $R_4$ is selected from $C_1$-$C_2$ alkyl, bromo, methylthio, $C_2$–$C_4$ polyfluoroalkenylthio, preferably having two fluorine atoms appended to a terminally double bonded carbon atom, formyl, $C_1$-$C_2$ alkoxycarbonyl, and dimethylphosphono;

(b) $R_1$ is lower alkyl, $R_2$ and $R_3$ are hydrogen, and $R_4$ is $C_1$-$C_2$ alkyl, chloro, or hydrogen when $R_1$ contains three or four carbon atoms;

(c) $R_1$ is halogen, $R_2$ is hydrogen or halogen, $R_3$ is hydrogen, and $R_4$ is selected from hydrogen when $R_2$ is halogen or when $R_2$ is hydrogen and $R_1$ is fluoro, 2-chloro, or 3-chloro; chloro when $R_1$ is a halogen other than chloro; $C_1$-$C_2$ alkyl; and benzoyl;

(d) $R_1$ is trifluoromethyl, $C_1$-$C_2$ alkoxy, $C_1$-$C_2$ polyfluoroalkoxy, polyfluoroethenyloxy, or phenoxy and $R_2$ is hydrogen or $R_1$ and $R_2$ together for a 13 $C_4H_4$— group bridging adjacent carbon ring atoms; $R_3$ is hydrogen, and $R_4$ is hydrogen or $C_1$-$C_2$ alkyl.

The compounds are especially effective against mites and against insect species of the order *Coleoptera*, such as Colorado potato beetle (*Leptinotarsa decemlineata*), as well as other foliage-feeding insect and acarid species, as described in more detail below. The compounds are also effectively employed against mosquito larvae (*Aedes aegypti*). Although the activity of the bithienyl compounds of this invention is dramatically affected by near ultraviolet light (320–400 nm), they are also active in the dark, e.g., against southern corn rootworm (*Diabrotica undecimpunctata howardi*) and the root-knot nematode (*Meloidogyne incognita*) when incorporated into the soil.

The compounds of the invention, in addition to being highly toxic to insects or acarids, exhibit extremely low phytotoxicity toward the plants on which such pests feed.

The bithienyl compounds of this invention are prepared by methods known in the art. For example, they are prepared according to procedures described by Wynberg and Metselaar, i Syn. Comm., 14, 1 (1984), Bedell, et al., i J. Org. Chem., 27, 2026 (1962), Stetter, et al., i J. Heterocyclic Chem., 14, 573 (1977), and Stetter, et al., i Chem. Ber., 114, 581 (1981). The procedure will be clarified by reference to the following specific Examples.

EXAMPLE 3

5'-Methyl-5-phenyl[2,2'-bithienyl]

Under a nitrogen atmosphere, a stirred solution of 10.0 grams (0.071 mole) of 2-acetyl-5-methylthiophene, 7.0 grams (0.086 mole) of dimethylamine hydrochloride, 2.5 grams of paraformaldehyde and 0.4 ml of concentrated hydrochloric acid in 10 ml of ethanol was heated under reflux for 16 hours. The reaction mixture was concentrated under reduced pressure to a residual solid. The solid was recrystallized from methanol-diethyl ether to give 10.9 grams of 3-dimethylamino-1-(5-methyl-2-thienyl)propan-1-one hydrochloride; m.p. 145°–147° C.

To a stirred suspension of 1.2 grams (0.025 mole) of sodium cyanide in 70 ml of dimethylformamide was added dropwise a solution of 5.2 grams (10 moles) of freshly distilled benzaldehyde in 40 ml of dimethylformamide. The complete addition required 20 minutes. The reaction mixture was stirred for one hour. Separately, while the mixture stirred, 10.0 grams (0.043 mole) of 3-dimethylamino-1-(5-methyl-2-thienyl)-propan-1-one hydrochloride was made alkaline in water with ammonium hydroxide, extracted with ethyl acetate, dried with sodium sulfate, filtered and concentrated. The so-prepared free Mannich base was dissolved in 40 ml of dimethylformamide and added dropwise to the benzaldehyde/sodium cyanide reaction mixture. The complete addition required one hour. The reaction mixture was stirred for an additional 16 hours, then concentrated under reduced pressure to a residual solid. The solid was taken up in water and extracted with three 100 ml portions of chloroform. The combined extracts were washed with water and dried with sodium sulfate. The organic layer was concentrated under reduced pressure to a solid residue. The solid was recrystallized from ethanol-water to give 8.3 grams of 1-phenyl-4-(5-methyl-2-thienyl)-1,4-butanedione; m.p. 122.5° C.

Under a nitrogen atmosphere a stirred solution of 3.0 grams (0.012 mole) of 1-phenyl-4-(5-methyl-2-thienyl)-1,4-butanedione and 3.0 grams (0.008 mole) of Lawesson3 s reagent in 100 ml of toluene was heated under reflux for one hour. The reaction mixture was concentrated under reduced pressure to a residue. The residue was subjected to column chromatography on silica gel using 15% methylene chloride-hexane as eluent. The appropriate fractions were combined and concentrated under reduced pressure to give 2.7 grams of 5'-methyl-5-phenyl[2,2'-bithienyl]; m.p. 102° C.

The nmr spectrum was consistent with the proposed structure.
Analysis:
Calc3 d for $C_{15}H_{12}S_2$: C 70.30; H 4.70;
Found: C 70.28; H 4.98.

EXAMPLE 64

5'-Bromo-5-[4-(1,1-dimethylethyl)phenyl][2,2'-bithienyl]

This compound was prepared in a manner analogous to Example 69, using 1.3 grams (0.0042 mole) of 5-[4-(1,1-dimethylethyl)phenyl][2,2'-bithienyl], 1.8 ml (0.046mole) of n-butyllithium (2.6M in hexanes), and 0.22 ml (0.0042 mole) of bromine in 30 ml of dry tetrahydrofuran. The yield of 5'-bromo-5-[4-(1,1-dimethylethyl)phenyl][2,2'-bithienyl] was 0.64 gram; m.p. 132°–136° C.

EXAMPLE 69

5'-Methyl-5-(4-methylthiophenyl)[2,2'-bithienyl]

Under a nitrogen atmosphere, a stirred solution of 0.82 gram (0.003 mole) of 5-(4-methylthiophenyl)[2,2'-bithienyl] in 100 ml of freshly distilled tetrahydrofuran was cooled to 0° C. and 1.4 ml of n-butyllithium (2.6M in hexanes) was added dropwise via syringe during a ten minute period. Upon completion of addition the reaction mixture stirred at 0° C. for 30 minutes, then at ambient temperature for three hours. The reaction mixture was recooled to 0° C. and an additional five drops of n-butyllithium was added. The reaction mixture stirred at 0° C. for one hour then 0.32 ml (0.0034 mole) of dimethylsulfate was added. Upon completion of addition the reaction mixture was stirred at ambient temperature for 16 hours. The reaction mixture was taken up in 70 ml of water and the organic layer was separated. The aqueous layer was washed with three 25 ml portions of chloroform. The organic layers were combined and washed, first with water, then with an aqueous solution saturated with sodium chloride. The organic layer was dried with sodium sulfate and filtered. The filtrate was concentrated under reduced pressure to yield 0.78 gram of 5'-methyl-5-(4-methylthiophenyl)[2,2'-bithienyl]; m.p. 145°–147° C.

EXAMPLE 74

5'-Methyl-4,5-diphenyl[2,2'-bithienyl]

A stirred solution of 2.2 grams (0.055 mole) of sodium hydroxide in 20 ml of ethanol was cooled to 0° C. and a mixture of 4.0 grams (0.03 mole) of 2-acetyl-5-methylthiophene and 3.1 grams (0.03 mole) of benzaldehyde in 5 ml of ethanol was added dropwise. Upon completion of addition the reaction mixture was allowed to warm to ambient temperature where it stirred for 16 hours. The reaction mixture was poured into aqueous 1N hydrochloric acid and extracted with methylene chloride. The extract was dried with sodium sulfate and filtered. The filtrate was concentrated under reduced pressure to yield 4.6 grams of 1-(5-methyl-2-thienyl)-3-phenyl-2-propen-1-one as a solid.

1,2-Diphenyl-4-(5-methyl-2-thienyl)-1,4-butanedione was prepared in a manner analogous to that described in Example 3. A yield of 6.0 grams of 1,2-diphenyl-4-(5-methyl-2-thienyl)-1,4-butanedione was obtained when 4.6 grams (0.02 mole) of 1-(5-methyl-2-thienyl)-3-phenyl-2-propen-1-one was reacted with 2.2 grams (0.02 mole) of benzaldehyde in the presence of 1.0 gram (0.02 mole) of sodium cyanide in 40 ml of dimethylformamide.

5'-Methyl-4,5-diphenyl[2,2'-bithienyl]was prepared in a manner analogous to that described in Example 3. A yield of 1.0 gram of 5'-methyl-4,5-diphenyl[2,2'-dithienyl] was obtained when 3.4 grams (0.01 mole) of 1,2-diphenyl-4-(5-methyl-2-thienyl)-1,4-butanedione was heated under reflux with 4.1 grams (0.01 mole) of Lawessons Reagent in toluene.

EXAMPLE 78

5'-(1-Methylethyl)-5-phenyl[2,2'-bithienyl]

A stirred suspension of 0.55 gram (0.0041 mole) of aluminum chloride in 40 ml of methylene chloride was cooled to 0° C., and a solution of 1.0 gram (0.0041 mole) of 5-phenyl[2,2'-bithienyl], 0.9 gram (0.005 mole) of 2-chloropropane in 40 ml of methylene chloride was added dropwise. Upon completion of addition the reaction mixture stirred at 0° C. for 30 minutes, then was allowed to warm to ambient temperature where it stirred for 16 hours. The reaction mixture was poured into a mixture of ice and aqueous 10% hydrochloric acid. The layers were separated and the aqueous phase was extracted with three 25 ml portions of diethyl ether. The organic layers were combined and the combination washed in succession with a solution of aqueous 5% sodium bicarbonate, water, and an aqueous solution saturated with sodium chloride. The organic layer was dried with sodium sulfate and filtered. The filtrate was concentrated under reduced pressure to a residue. The residue was subjected to column chromatography on silica gel. Elution was accomplished with 100% hexane. The appropriate fractions were combined and concentrated under reduced pressure to yield 0.7 gram of 5'-(1-methylethyl)-5-phenyl[2,2'-bithienyl]; m.p. 104°–106° C.

EXAMPLE 79

5'-Methoxy-5-(4-methylphenyl)[2,2'-bithienyl]

A solution of 1.5 grams (0.004 mole) of 5'-bromo-5-(4-methylphenyl) [2,2'-bithienyl] (prepared as in Example 64) in 25 ml of dry tetrahydrofuran was stirred, and 0.24 gram (0.0044 mole) of sodium methoxide in methanol was added. Upon completion of addition the reaction mixture was stirred at ambient temperature for three hours, then was heated under reflux for 16 hours. The reaction mixture was cooled and 50 ml of aqueous 10% hydrochloric acid was added. The mixture was extracted with methylene chloride and the extract dried with sodium sulfate. The mixture was filtered and the filtrate concentrated under reduced pressure to a residue. The residue was subjected to column chromatography on silica gel. Elution was accomplished with 25% methylene chloride in hexane. The appropriate fractions were combined and concentrated under reduced pressure to yield 0.6 gram of 5'-methoxy-5-(4-methylphenyl)[2,2'-bithienyl], m.p. 108°–111° C.

EXAMPLE 81

5'-Methylthio-5-(4-fluorophenyl)[2,2'-bithienyl]

This compound was prepared in a manner analogous to Example 69 using 1.5 gram (0.006 mole) of 5-(4-fluorophenyl)[2,2'-bithienyl]2.5 ml (0.006 mole) of n-butyllithium (2.6M in hexanes) and 0.36 gram (0.006 mole) of methyl disulfide in 100 ml of dry diethyl ether. The yield of 5'-methylthio-5-(4-fluorophenyl)[2,2'-bithienyl]was 2.0 grams as a solid.

In an alternate method, the lithium salt of 5-(4-fluorophenyl)[2,2'-bithienyl] was reacted at −78° C. with an excess of sulfur in dry tetrahydrofuran to yield the corresponding 5'-mercapto-5-(4-fluorophenyl)[2,2'-bithienyl], which was in turn reacted in situ with an equivalent amount of methyl iodide to yield 5'-methyl-thio-5-(4-fluorophenyl) [2,2'-bithienyl].

EXAMPLE 82

5'-Methylsulfinyl-5-(4-fluorophenyl)[2,2'-bithienyl]

A solution of 2.0 grams (0.0065 mole) of 5'-methylthio-5-(4-fluorophenyl) [2,2'-bithienyl] (prepared as in Example 81) in 65 ml of methylene chloride was stirred, and 1.5 grams (0.0065 mole) of m-chloroperoxybenzoic acid was slowly added. Upon completion of addition the reaction mixture was heated under reflux for 60 hours, then cooled and diluted with 35 ml of methylene chloride. The solution was washed repeatedly with an aqueous 10% sodium hydroxide solution. The organic layer was dried with sodium sulfate and filtered. The filtrate was concentrated under reduced pressure to a residue. The residue was subjected to column chromatography on silica gel. Elution was accomplished using 25% methylene chloride in hexane. The appropriate fractions were combined and concentrated under reduced pressure to yield a residue. The residue was slurried in chloroform and filtered to remove insoluble material. The filtrate was concentrated under reduced pressure to yield 0.3 gram of 5'-methylsulfinyl-5-(4-fluorophenyl)-[2,2'-bithienyl]; m.p. 153°–157° C.

EXAMPLE 84

5'-Formyl-5-phenyl[2,2'-bithienyl]

This compound was prepared in a manner analogous to Example 69, using 2.0 grams (0.0083 mole) of 5-phenyl-[2,2'-bithienyl], 3.2 ml (0.0083 mole) of n-butyllithium (2.6M in hexanes), and 0.66 gram (0.0091 mole) of dimethylformamide in 50 ml of dry tetrahydrofuran. The yield of 5'-formyl-5-phenyl[2,2'-bithienyl] was 0.1 gram; m.p. 119°–121° C.

EXAMPLE 88

5'-(Ethoxycarbonyl)-5-phenyl[2,2'-bithienyl]

This compound was prepared in a manner analogous to Example 69 using 2.0 grams (0.083 mole) of 5-phenyl-[2,2'-bithienyl], 3.2 ml (0.0083 mole) of n-buthyl-lithium (2.6M in hexanes), and 1.0 gram (0.0092 mole) of ethyl chloroformate in 50 ml of dry tetrahydrofuran The yield of 5'-(ethoxycarbonyl)-5-phenyl[2,2'-bithienyl]-was 0.9 gram; m.p. 113–115° C.

EXAMPLE 89

5'-Benzoyl-5-(4-chlorophenyl)[2,2'-bithienyl]

This compound was prepared in a manner analogous to that of Example 78, using 2.5 grams (0.009 mole) of 5-(4-chlorophenyl)[2,2'-bithienyl], 1.3 grams (0.0091 mole) of aluminum chloride in 50 ml of methylene chloride, differing only in that the aluminum chloride was added to a solution of the bithienyl and the benzoyl chloride in methylene chloride at 0° C. The yield of 5'-benzoyl-5-(4-chlorophenyl)[2,2'-bithienyl] was 0.5 gram; m.p. 165°–175° C.

EXAMPLE 92

Dimethyl [5-phenyl[2,2'-bithien-5'-yl]] phosphonate

This compound was prepared in a manner analogous to Example 69 using 2.0 grams (0.0083 mole) of 5-phenyl-[2,2'-bithienyl], 3.2 grams (0.0083 mole) of n-butyl-lithium (2.6 M in hexanes), and 1.3 grams (0.0091 mole) of dimethyl chlorophosphonate in 50 ml of dry tetrahydrofuran. The yield of dimethyl [5-phenyl[2,2'-bithien-5'-yl]]phosphonate was 0.61 gram; m.p. 83°–85° C.

The following additional bithienyl compounds are prepared by similar techniques:

| Ex. | Name | m.p. (°C.) |
|---|---|---|
| 1 | 5-phenyl[2,2'-bithienyl] | 119.5–121.5 |
| 2 | 4'-methyl-5-phenyl-[2,2'-bithienyl] | 69–71 |
| 4 | 5-(4-chlorophenyl)-[2,2'-bithienyl] | 165–167 |
| 5 | 5-chloro-5'-(4-chlorophenyl)[2,2'-bithienyl] | 145–147 |
| 6 | 3'-methyl-5-(4-chlorophenyl)[2,2'-bithienyl] | 79–81 |
| 7 | 5'-methyl-5-(4-chlorophenyl)[2,2'-bithienyl] | 170–172 |
| 8 | 5-(4-chlorophenyl)-2,2',3,2''-terthienyl | liquid |
| 9 | 5-(4-fluorophenyl)-[2,2'-bithienyl] | 141–142 |
| 10 | 5'-chloro-5-(4-fluorophenyl)[2,2'-bithienyl] | 125–127 |
| 11 | 5'-methyl-5-(4-fluorophenyl)[2,2'-bithienyl] | 142–144 |
| 12 | 5-(4-methylphenyl)-[2,2'-bithienyl] | 129.5–131 |
| 13 | 5-(4-trifluoromethylphenyl)[2,2'-bithienyl] | 174–176 |
| 14 | 5-(4-methoxyphenyl)-[2,2'-bithienyl] | 158–160 |
| 21 | 5-phenyl[2,3'-bithienyl] | 155–157 |
| 22 | 5-(4-trifluoromethylphenyl)-[2,3'-bithienyl] | 174–176 |
| 23 | 4-phenyl[3,2'-bithienyl] | liquid |
| 25 | 5-(4-chlorophenyl)-2-phenyl[3,2'-bithienyl] | 120–121 |
| 28 | 5'-methyl-5-(4-methylphenyl)[2,2'-bithienyl] | 100–101 |
| 29 | 5'-chloro-5-phenyl-[2,2'-bithienyl] | 138–140 |
| 30 | 5'-bromo-5-phenyl-[2,2'-bithienyl] | 128–130 |
| 31 | 5'-methyl-5-(4-methoxyphenyl)[2,2'-bithienyl] | 160–162 |
| 32 | 5'-ethyl-5-phenyl-[2,2'-bithienyl] | 79–81 |
| 33 | 5-(3,4-difluorophenyl)-[2,2'-bithienyl] | 140–142 |
| 34 | 5'-methyl-5-(3,4-dichlorophenyl)[2,2'-bithienyl] | 126–128 |
| 35 | 5'-methyl-5-(4-trifluoromethylphenyl)-[2,2'-bithienyl] | 194–196 |
| 36 | 3-phenyl-5-(4-chlorophenyl)[2,2'-bithienyl] | 74–77 |
| 37 | 5'-methyl-5-(4-bromophenyl)[2,2'-bithienyl] | 177–179 |
| 38 | 5'-methyl-4-phenyl-5-(4-chlorophenyl)-[2,2'-bithienyl] | 98–101 |
| 39 | 4,5'-dimethyl-5-(4-chlorophenyl)-[2,2'-bithienyl] | |
| 40 | 5'-methyl-3-(1-methylethyl)-5-(4-chlorophenyl)-[2,2'-bithienyl] | |
| 41 | 5'-chloromethyl-5-(4-chlorophenyl)-[2,2'-bithienyl] | |
| 42 | 5'-trifluoromethyl-5-(4-chlorophenyl)-[2,2'-bithienyl] | |
| 43 | 3,5'-dimethyl-5-(4-chlorophenyl)-[2,2'-bithienyl] | |
| 44 | 5'-methyl-5-[4-(1,1,2,2-tetrafluoroethoxy)phenyl]-[2,2'-bithienyl] | |
| 45 | 5-(2-chlorophenyl)[2,2'-bithienyl[ | liquid |
| 46 | 5-(3-chlorophenyl)[2,2'-bithienyl] | 98–99.5 |
| 47 | 5-(4-ethylphenyl)[2,2'-bithienyl] | 112–113 |
| 48 | 5-[4-(1,1-dimethylethyl)-phenyl][2,2'-bithienyl] | 102–104 |
| 49 | 5-(3-trifluoromethylphenyl)-[2,2'-bithienyl] | 90–92 |
| 50 | 5-[3-(1,1,2,2-tetrafluoroethoxy)phenyl][2,2'-bithienyl] | 80–82 |
| 51 | 5-[4-(1,1,2,2-tetrafluoroethoxy)phenyl][2,2'-bithienyl] | 144–146 |
| 52 | 5-[4-(1,2,2-trifluoroethenoxy)-phenyl][2,2'-bithienyl] | 136–138 |
| 53 | 5-(4-methylthiophenyl)[2,2'-bithienyl] | |
| 54 | 5-(2-napthyl)[2,2'-bithienyl] | 197–199 |
| 56 | 4-(2,6-difluorophenyl)-5-phenyl[2,2'-bithienyl] | liquid |
| 57 | 5'-chloro-5-(4-methylphenyl)-[2,2'-bithienyl] | 145–146.5 |
| 58 | 5'-chloro-5-(4-ethylphenyl)-[2,2'-bithienyl] | 143–145 |
| 59 | 5'-chloro-4,5-diphenyl[2,2'-bithienyl] | liquid |
| 60 | 5'-chloro-4-(4-methylphenyl)-5-phenyl[2,2'-bithienyl] | liquid |
| 61 | 5'-chloro-4-(4-methoxyphenyl)-5-phenyl[2,2'-bithienyl] | liquid |
| 62 | 5'-chloro-5-(4-chlorophenyl)-4-phenyl[2,2'-bithienyl] | |
| 63 | 5'-bromo-5-(4-methylphenyl)-[2,2'-bithienyl] | |
| 65 | 5'-methyl-5-(3-chlorophenyl)-[2,2'-bithienyl] | 98–99 |
| 66 | 5'-methyl-5-(4-difluoromethoxyphenyl)[2,2'-bithienyl] | 171–172 |
| 67 | 5'-methyl-5-(4-trifluoromethoxyphenyl)[2,2'-bithienyl] | 146–148 |
| 68 | 5'-methyl-5-[3-(1,1,2,2-tetrafluoroethoxy)phenyl][2,2'-bithienyl] | 96–98 |
| 70 | 5'-methyl-5-(4-methylsulfinylphenyl)[2,2'-bithienyl] | 171–179 |
| 71 | 5'-methyl-5-(4-nitrophenyl)-[2,2'-bithienyl] | 155–157 |
| 72 | 5'-methyl-5-(4-phenoxyphenyl)-[2,2'-bithienyl] | 126–128 |
| 73 | 5'-methyl-5-(2-naphthyl)[2,2'-bithienyl] | 144–145 |
| 75 | 5'-methyl-5-(4-chlorophenyl)-4-phenyl[2,2'-bithienyl] | |
| 76 | 5'-methyl-4,5-di(4-chlorophenyl)[2,2'-bithienyl] | 120–121 |
| 77 | 5'-ethyl-5-(4-difluoromethoxyphenyl)[2,2'-bithienyl] | 157–158 |
| 80 | 5'-methylthio-5-phenyl-[2,2'-bithienyl] | 119–120 |
| 83 | 5'-(3,4,4-trifluoro-3-butenylthio)-5-phenyl[2,2'-bithienyl] | 75–77 |
| 85 | 5'-formyl-5-(4-methylthiophenyl)[2,2'-bithienyl] | 145–148 |
| 86 | 5'-acetyl-5-(4-methylthiophenyl)[2,2'-bithienyl] | 144–149 |
| 87 | 5'-acetyl-5-(4-methylsulfonylphenyl)[2,2'-bithienyl] | 225–229 |
| 90 | 5'-benzoyl-5-(4-trifluoromethylphenyl)[2,2'-bithienyl] | 141–144 |
| 91 | 5'-benzoyl-5-[4-(1,1-dimethylethyl)phenyl][2,2'-bithienyl] | 171–172 |
| 93 | 5'-nitro-5-phenyl[2,2'-bithienyl] | 158–160 |

In the normal use of the insecticidal and acaricidal bithienyl compounds of the present invention, the bithienyl compounds usually will not be employed free from admixture or dilution, but ordinarily will be used in a suitable formulated composition compatible with the method of application and comprising an insecticidally or acaricidally effective amount of bithienyl compound. The bithienyl compounds of this invention, like most pesticidal agents, may be blended with the agriculturally acceptable surface-active agents and carriers normally employed for facilitating the dispersion of active ingredients, recognizing the accepted fact that the formulation and mode of application of an insecticide may affect the activity of the material. The present bithienyl compounds may be applied, for example, as sprays, dusts, or granules to the area where pest control is desired, the type of application varying of course with the pest and the environment. Thus, the bithienyl compounds of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the bithienyl compounds. The granule particles are relatively large, a diameter of about 400–2500 microns typically. The particles are either impregnated with the bithienyl compound from solution or coated with the bithienyl compound, adhesive sometimes being employed. Granules generally contain 0.05–10%, preferably 0.5–5%, active ingredient as the insecticidally effective amount.

Dusts are admixtures of the bithienyl compounds with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide or acaricide. These finely divided solids have an average particle size of less than about 50 microns. A typical dust formulation useful for controlling insects contains 1 part of bithienyl compound, such as 4′-methyl-5-phenyl[2,2′-bithienyl], and 99parts of talc.

The bithienyl compounds of the present invention may be made into liquid concentrates by dissolution or emulsification in suitable liquids and into solid concentrates by admixture with talc, clays, and other known solid carriers used in the pesticide art. The concentrates are compositions containing, as an insecticidally effective amount, about 5–50% bithienyl compound and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

A typical 50% wettable powder formulation would consist of 50.0% (wt/wt) of 5′-methyl-5-(4-chlorophenyl)[2,2′-bithienyl], 22.0% attapulgite diluent, 22.0% kaolin diluent, and 6.0% sodium salts of sulfonated Kraft lignin emulsifier.

Typical carriers for solid concentrates (also called wettable powders) include fuller3 s earth, clays, silicas, and other highly absorbent, readily wetted inorganic diluents. A solid concentrate formulation useful for controlling insects or acarids contains 1.5 parts each of sodium lignosulfonate and sodium laurylsulfate as wetting agents, 25 parts of 5′-methyl-5-phenyl[2,2′-bithienyl], and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the bithienyl compound with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

A typical 50 gram per liter emulsifiable concentrate formulation would consist of 5.90% (wt/wt) of 5′-methyl-5-phenyl[2,2′-bithienyl]; as emulsifiers: 1.80% of a blend of the calcium salt of dodecylbenzene sulfonate and a nonionic 6-molar ethylene oxide condensation product of nonylphenol, 2.70% of a blend of the calcium salt of dodecylbenzene sulfonate and a nonionic 30-molar ethylene oxide condensation product of nonylphenol, 1.50% of a nonionic paste of polyalkylene glycol ether; and 88.10% refined xylene solvent.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal or acaricidal composition.

Other useful formulations include simple solutions of the active ingredient in a solvent in which it is completely soluble at the desired concentration, such as acetone or other organic solvents.

An insecticidally or acaricidally effective amount of bithienyl compound in an insecticidal or acaricidal composition diluted for application is normally in the range of about 0.001% to about 8% by weight. Many variations of spraying and dusting compositions known in the art may be used by substituting the bithienyl compounds of this invention into compositions known or apparent in the art.

The insecticidal or acaricidal compositions of this invention may be formulated with other active ingredients, including other insecticides, nematicides, acaricides, fungicides, plant growth regulators, fertilizers, etc. In using the compositions to control insects or acarids, it is only necessary that an insecticidally or acaricidally effective amount of bithienyl compound be applied to the locus where control is desired. Such locus may, e.g., be the insects themselves, plants upon which the insects feed, or the insect habitat. When the locus is soil, e.g., soil in which agricultural crops are or will be planted, the active compound may be applied to and optionally incorporated into the soil. For most applications, an insecticidally or acaricidally effective amount will be about 50 to 750 g per hectare, preferably 150 g to 500 g per hectare.

The insecticidal and acaricidal activity of the bithienyl compounds whose preparation is described above was evaluated as follows:

The bithienyl compounds were tested for insecticidal and acaricidal activity under near ultraviolet light (wavelength 320–400 nanometers) at an intensity of 1600–2400 microwatts/cm2 using test procedures adapted to the various organisms in the test. Regardless of the organism, foliage of whole plants or foliage removed from whole plants was sprayed to runoff with a 10% acetone-0.25% octylpohenoxypolyethoxyethanol-water solution containing up to 200 ppm of the test compound.

Leaves infested with adult twospotted spider mites (*Tetranychus urticae*) were removed from culture plants and cut into segments containing 50–↓ female mites. Each segment was placed on the upper leaf surface of a whole pinto bean (*Phaseolus vulgaris*) plant. After the mites had migrated to the under surfaces of the leaves, the leaf segments used to infest were removed and each plant sprayed with test chemical as described above. After the plants had dried, the entire plant and pot were placed in metal trays in a hood. A supply of water in the tray kept the plants turgid. Tests were conducted against both susceptible and phosphate resistant strains.

In tests utilizing pea aphid (*Acyrthosiphon pisum*), whole fava bean (*Vicia faba*) plants were sprayed with test chemical and allowed to dry as described above. Individual test plants in their pots were placed in 48 ounce waxed containers. Ten adult pea aphids, selected for uniformity of size and vigor were counted into each container. Each container was covered with a glass petri dish and placed on a rack where they were held as described above.

In tests utilizing the Mexican bean beetle (*Epilachna varivestis*), cabbage looper (*Trichoplusia ni*), or the southern armyworm (*Spodoptera eridania*), the pinto bean test plants were sprayed with test chemical and allowed to dry as previously described. Each test plant was cut off at the soil line and the stem was pushed through a small diameter hole punched in the bottom of an eight ounce waxed container. Ten first instar Mexican bean beetle, cabbage looper, or southern armyworm larvae were counted into each container. Each container was covered with a glass petri dish and, with the plant stem protruding from the bottom, placed on a holding rack which allowed the stem to remain in water throughout the exposure period.

The test results were collected and recorded at the end of a 24 hour (Examples 35–93) or 48 hour exposure period. These data appear in Table 1.

TABLE 1

| | | Foliar Test Results | | | | | |
| | | | Insect Species (% Kill) | | | | |
| Cpd. | Application Rate (ppm) | TSM-$S^a$ | TSM-$R^b$ | SAW | MBB | PA | CL |
|---|---|---|---|---|---|---|---|
| 1 | 100 | 100 | 86 | 0 | 95 | 45 | |
| 2 | 100 | | 100 | 0 | 80 | 5 | |
|   | 20 | 100 | | | | | |
| 3 | 200 | | | 0 | 85 | | |
|   | 32 | | 100 | | | | |
|   | 5 | 98 | | | | | |
| 4 | 100 | 100 | 100 | 0 | 55 | 0 | |
| 5 | 20 | 100 | | | | | |
| 6 | 200 | | | 80 | 80 | 5 | |
|   | 50 | 100 | | | | | |
| 7 | 200 | | | | | 20 | |
|   | 128 | | | 12 | | | |
|   | 100 | | 100 | | 75 | 0 | |

TABLE 1-continued

| | | Foliar Test Results | | | | | |
| | | | Insect Species (% Kill) | | | | |
| Cpd. | Application Rate (ppm) | TSM-$S^a$ | TSM-$R^b$ | SAW | MBB | PA | CL |
|---|---|---|---|---|---|---|---|
|   | 20 | 97 | | | | | |
| 8 | 20 | 100 | | | | | |
| 9 | 200 | | | 0 | | 10 | |
|   | 50 | 100 | $100^c$ | 70 | | | |
| 10 | 50 | 100 | | | | | |
| 11 | 100 | 100 | | | | | |
| 12 | 50 | 100 | | | | | |
| 13 | 100 | | 100 | 5 | 95 | 0 | |
|   | 20 | 100 | | | | | |
| 14 | 100 | 100 | | | | | |
| 21 | 200 | | | | 100 | 0 | |
|   | 4 | 28 | | | | | |
| 22 | 100 | 100 | | | | | |
| 23 | 100 | 42 | | | | | |
| 25 | 20 | 100 | | | | | |
| 28 | 50 | 100 | | | | | |
| 29 | 50 | 100 | | | | | |
| 30 | 50 | 100 | | | | | |
| 31 | 50 | 100 | | | | | |
| 32 | 50 | 100 | | | | | |
| 33 | 50 | 100 | | | | | |
| 34 | 50 | 100 | | | | | |
| 35 | 200 | | | | | | 5 |
|   | 1 | 41 | 48 | | | | |
| 36 | 200 | | | | | | 0 |
|   | 5 | 97 | 87 | | | | |
| 37 | 200 | | | | | | 5 |
|   | 10 | 100 | 46 | | | | |
| 44 | 200 | | | | | | 0 |
|   | 50 | 100 | 100 | | | | |
| 45 | 200 | | | | | | 10 |
|   | 5 | 100 | 89 | | | | |
| 46 | 200 | | | | | | 50 |
|   | 50 | 100 | 100 | | | | |
| 47 | 200 | | | | | | 0 |
|   | 50 | 100 | 91 | | | | |
| 48 | 200 | | | | | | 0 |
|   | 50 | 100 | 97 | | | | |
| 49 | 100 | 100 | 100 | | | | |
| 50 | 200 | | | | | | 5 |
|   | 50 | 98 | 100 | | | | |
| 51 | 200 | | | | | | 0 |
|   | 50 | 100 | 100 | | | | |
| 52 | 200 | | | | | | 0 |
|   | 50 | 100 | 99 | | | | |
| 53 | 200 | | | | | | 0 |
|   | 50 | 0 | | | | | |
| 54 | 100 | | | | | | 0 |
|   | 50 | 97 | 0 | | | | |
| 55 | 50 | 91 | 0 | | 0 | | |
| 56 | 200 | | | | | | 0 |
|   | 50 | 20 | | | | | |
| 57 | 200 | | | | | | 0 |
|   | 50 | 100 | 90 | | | | |
| 58 | 200 | | | | | | 0 |
|   | 50 | 100 | 97 | | | | |
| 59 | 200 | | | | | | 0 |
|   | 50 | 95 | | | | | |
| 60 | 200 | | | | | | 25 |
|   | 50 | 98 | | | | | |
| 61 | 200 | | | | | | 0 |
|   | 50 | 100 | | | | | |
| 62 | 200 | | | | | | 0 |
|   | 50 | 49 | | | | | |
| 63 | 200 | | | | | | 0 |
|   | 50 | 22 | | | | | |
| 64 | 200 | | | | 0 | | |
|   | 50 | 100 | 80 | | | | |
| 65 | 200 | | | | | | 30 |
|   | 5 | 100 | 21 | | | | |
| 66 | 200 | | | | | | 5 |
|   | 50 | 100 | 64 | | | | |
| 67 | 200 | | | | | | 10 |
|   | 1 | 91 | 35 | | | | |
| 68 | 200 | | | | | | 0 |
|   | 50 | 100 | 100 | | | | |
| 69 | 200 | | | | | | 0 |

TABLE 1-continued

Foliar Test Results

| Cpd. | Application Rate (ppm) | TSM-S[a] | TSM-R[b] | SAW | MBB | PA | CL |
|---|---|---|---|---|---|---|---|
| 70 | 50 | 95 | | | | | |
| | 200 | | | | | | 0 |
| 71 | 50 | 75 | | | | | |
| | 200 | | | | | | 0 |
| 72 | 50 | 23 | | | | | |
| | 200 | | | | | | 0 |
| 73 | 50 | 100 | 90 | | | | |
| | 100 | | | | 0 | | |
| 74 | 50 | 96 | 100 | | 0 | | |
| | 200 | | | | | | 0 |
| 75 | 50 | 96 | | | | | |
| | 200 | | | | | | 0 |
| 76 | 20 | 93 | | | | | |
| | 200 | | | | | | 0 |
| 77 | 50 | 42 | | | | | |
| | 100 | | 93 | | 45 | | |
| 78 | 20 | 95 | | | | | |
| | 200 | | | | 5 | | |
| 79 | 50 | 100 | | | | | |
| | 200 | | | | | | 0 |
| 80 | 50 | 99 | | | | | |
| 81 | 50 | 100 | 95 | | 0 | | |
| | 200 | | | | 0 | | |
| 82 | 50 | 100 | | | | | |
| | 200 | | | | 20 | | |
| 83 | 50 | 100 | 74 | | | | |
| | 100 | | 100 | | 0 | | |
| 84 | 5 | 97 | 3 | | | | 25 |
| | 200 | | | | | | |
| 85 | 5 | 92 | | | | | |
| | 200 | | | | 0 | | |
| 86 | 50 | 100 | 100 | | | | |
| | 200 | | | | 0 | | |
| 87 | 50 | 67 | | | | | |
| | 200 | | | | 0 | | |
| 88 | 50 | 16 | | | | | |
| | 100 | | 100 | | | | |
| 89 | 100 | | 100 | | 0 | | |
| 90 | 200 | | | | 0 | | |
| 91 | 50 | 100 | | | | | |
| | 200 | | | | 0 | | |
| 92 | 50 | 99 | | | | | 5 |
| | 100 | | 100 | | | | |
| 93 | 50 | 100 | 40 | | | | |
| | 200 | | | | | | 0 |
| | 50 | 3 | | | | | |

[a] susceptible
[b] resistant
[c] 72 hr. exposure

What is claimed is:

1. A compound of the formula:

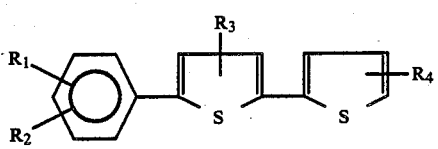

in which:
(a) $R_1$, $R_2$, and $R_3$ are hydrogen and $R_4$ is selected from $C_1-C_2$ alkyl, bromo, methylthio, $C_2-C_4$ polyfluoroalkenylthio having two fluorine atoms appended to a terminally double bonded carbon atom, formyl, $C_1-C_2$ alkoxycarbonyl, and dimethylphosphono;
(b) $R_1$ is lower alkyl, $R_2$ and $R_3$ are hydrogen, and $R_4$ is $C_1-C_2$ alkyl, chloro, or hydrogen when $R_1$ contains three or four carbon atoms;
(c) $R_1$ is halogen, $R_2$ is hydrogen or halogen, $R_3$ is hydrogen, and $R_4$ is selected from hydrogen when $R_2$ is halogen or when $R_2$ is hydrogen and $R_1$ is fluoro, 2-chloro, or 3-chloro; chloro when $R_1$ is a halogen other than chloro; $C_1-C_2$ alkyl; and benzoyl;
(d) $R_1$ is trifluoromethyl, $C_1-C_2$ alkoxy, $C_1-C_2$ polyfluoroalkoxy, polyfluoroethenyloxy, or phenoxy and $R_2$ is hydrogen or $R_1$ and $R_2$ together for a 13 $C_4H_4$— group bridging adjacent carbon ring atoms; $R_3$ is hydrogen, and $R_4$ is hydrogen or $C_1-C_2$ alkyl.

2. The compound of claim 1, 5'-methyl-5-phenyl.

3. The compound of claim 1, 5'-methyl-5-(4-chlorophenyl) [2,2'-bithienyl].

4. The compound of claim 1, 5'-(4-trifluoromethylphenyl) [2,2'-bithienyl].

5. The compound of claim 1, 5'-methyl-5-(4-trifluoromethoxyphenyl)[2,2'-bithienyl].

6. An acaricidal composition comprising an agriculturally acceptable carrier and an acaricidally effective amount of a compound of claim 1.

7. The acaricidal composition of claim 6 in which the active ingredient is selected from 5'-methyl-5-phenyl-[2,2'-bithienyl]; 5-methyl-5-(4-chlorophenyl) 2,2[-bithienyl]; 5'-(4-trifluoromethylphenyl)[2,2'bithienyl]; and 5-(4-trifluoromethoxyphenyl)[2,2-bithienyl].

* * * * *